United States Patent [19]

Dragan

[11] Patent Number: 4,457,712
[45] Date of Patent: Jul. 3, 1984

[54] DENTAL SYRINGE

[76] Inventor: William B. Dragan, 85 Burr Street, Easton, Conn. 06430

[21] Appl. No.: 251,278

[22] Filed: Apr. 6, 1981

Related U.S. Application Data

[63] Continuation-in-part of Ser. No. 93,059, Nov. 13, 1979, abandoned.

[51] Int. Cl.³ .............................................. A61C 5/04
[52] U.S. Cl. .................................... 433/90; 222/391; 222/569; 604/211
[58] Field of Search ...................... 433/90, 89, 81, 72; 604/211; 222/390, 391, 569, 287, 309, 326, 473, 472

[56] References Cited

U.S. PATENT DOCUMENTS

| | | | |
|---|---|---|---|
| 742,446 | 10/1903 | Kelly | 433/90 |
| 2,086,462 | 7/1937 | Bost | 433/90 |
| 2,102,591 | 12/1937 | Hagemeier | 433/90 |
| 2,142,780 | 1/1939 | Fortney | 433/90 |
| 2,736,315 | 2/1956 | Feeney | 604/211 |
| 2,884,877 | 5/1959 | Nalbone et al. | 222/391 |
| 3,141,583 | 7/1964 | Mapel et al. | 222/391 |
| 3,248,950 | 5/1966 | Pursell et al. | 222/309 |
| 3,322,307 | 5/1967 | Fraser | 222/391 |
| 3,816,921 | 6/1974 | Malmin | 433/90 |
| 4,265,618 | 5/1981 | Herskovitz et al. | 433/81 |

FOREIGN PATENT DOCUMENTS

| | | | |
|---|---|---|---|
| 324300 | 3/1903 | France | 128/234 |
| 671078 | 12/1929 | France | 222/390 |
| 1364845 | 6/1962 | France | 433/90 |
| 327859 | 4/1930 | United Kingdom | 221/47 |
| 1456650 | 11/1976 | United Kingdom | 433/90 |

*Primary Examiner*—John J. Wilson
*Attorney, Agent, or Firm*—Arthur T. Fattibene

[57] ABSTRACT

This disclosure is directed to a dental syringe having a barrel and a plunger reciprocally mounted within the barrel which is rendered displaceable so as to extrude a dental root canal through a relatively small bore hyperdermic type needle so as to place the material into the root canals of a tooth during a root canal procedure. In another form of the invention, the dental syringe is modified for use in extruding an impression forming material into the small areas around the gums so as to remove the air prior to the application of the bulk of the impression forming material to complete the impression.

4 Claims, 18 Drawing Figures

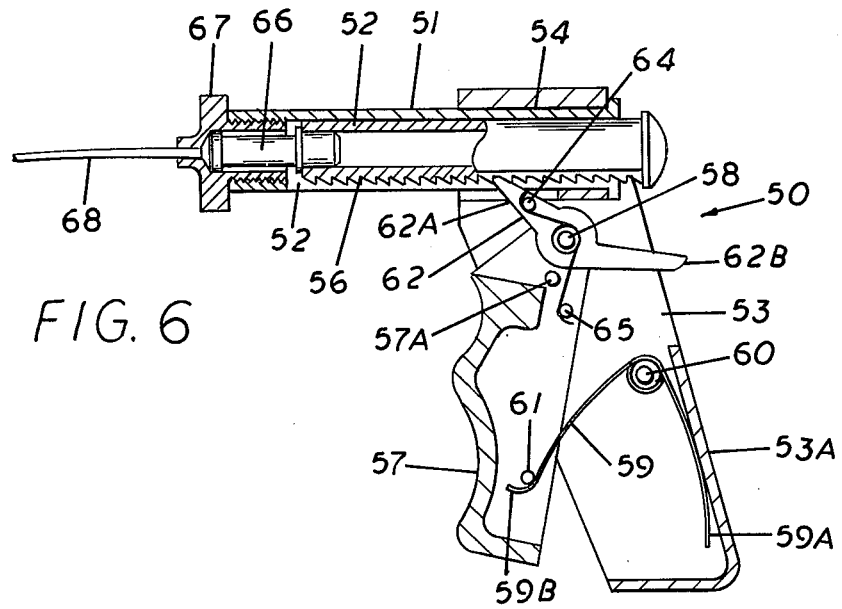
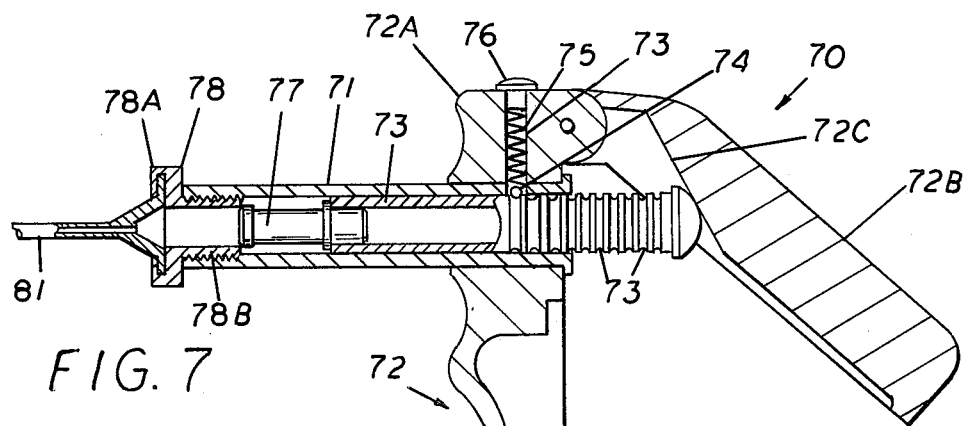
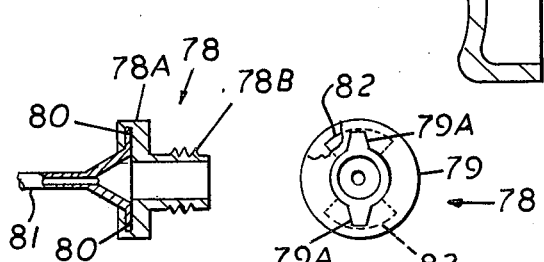
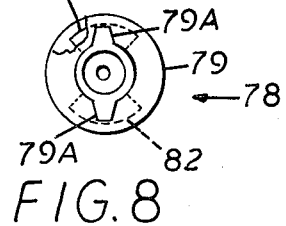
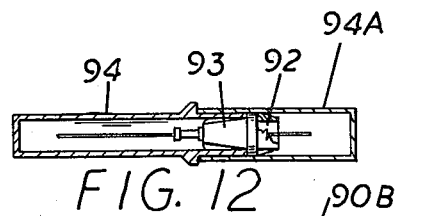
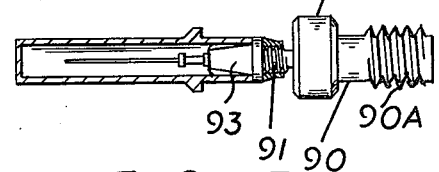
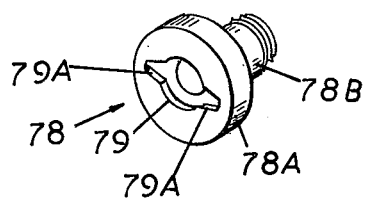
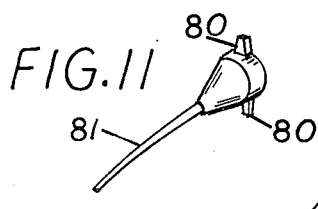
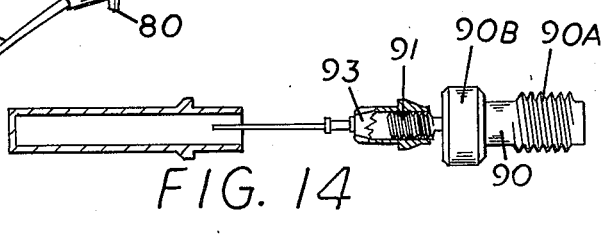

DENTAL SYRINGE

RELATED APPLICATIONS

This application is a continuation-in-part application of a co-pending application Ser. No. 093,059 filed Nov. 13, 1979, now abandoned, entitled DENTAL SYRINGE.

This application is also directed to improvements in the art of dental syringes of the type disclosed in my prior U.S. Pat. Nos. 3,581,399; 3,900,954 and 4,198,756.

PROBLEM

Heretofore, a root canal procedure was a tedius and time consuming operation. After the root canal of a tooth has been cleaned and properly desensitized, the root canal had to be filled to complete the procedure. Generally, this was attained by spinning root canal cement into the canal and thereafter placing very fine "points" in the canal to fill the void. More recently, root canals have been filled with root canal resin type material. However, such root canal resin material is difficult to handle, particularly in attempting to pack such material into the root canals of a tooth.

Another dental procedure which required care is the forming of an impression. It was heretofore difficult to pack a rubber base impression compound or other impression material into the samll areas around the gums so as to remove the air therefrom prior to placing the bulk of the impression material about the tooth to complete the impression.

OBJECTS

It is, therefore, an object of this invention to provide a dental syringe which will facillitate the filling of a root canal with a root canal resin.

Another object is to provide a root canal syringe which is capable of extruding a relatively viscous root canal material into a root canal.

Another object is to provide a root canal syringe having a needle like nozzle or tip which is rendered readily disposable.

Another object is to provide an improved dental syringe in which the amount of material being extruded thereby can be gaged or controlled.

Another object is to provide a dental syringe in which the dispensing tip is sufficiently small so as to direct the filling material into the small root canals of a tooth and which is capable of imparting the necessary force to extrude the filling material through the miniscule bore of the dispensing tip by the application of nominal pressure.

Another object is to provide a dental syringe by which the difficulty and time entailed in performing a root canal procedure can be greatly reduced and whereby the quality of the end result can be enhanced.

Another object is to provide a dental syringe having an adjustable limiting or stop means which is rendered readily accessible to the dentist and whereby the adjusting of the stop means can be effected during an extruding operation to variably control the amount of material extruded.

Another object is to provide a dental syringe wherein a dentist can accurately and positively dispense varying predetermined amounts of dental material during a dental restorative procedure in a manner whereby the amount of material dispensed can be varied as the material is extruded.

Another object is to provide a dental syringe which can be readily adapted to use in variable dental procedures.

Another object is to provide a dental syringe which is relatively simple, inexpensive and reliable in use.

BRIEF SUMMARY OF THE INVENTION

The foregoing objects and other features and advantages are attained by a dental syringe which comprises a tubular barrel having open front and rear ends in which a plunger is inserted through the rear open end and is reciprocally mounted within the barrel. A fitting defining a reservoir for containing a supply of dental filling material is fitted to the open front end of the barrel. Connected to the reservoir is a long hyperdermic type dispensing needle by which the material being extruded therefrom is directed into the small root canal of a tooth. To insure proper extrusion of the relatively viscous filling material through the miniscule bore of the dispensing needle, a handle means is provided by which a mechanical advantage is applied onto the plunger when the handle is actuated with nominal force only. The dental syringe also includes a structure by which the amount of material being extruded can be noted and controlled. This is attained by incorporating a gauging means either on the plunger whereby the linear displacement of the plunger is rendered proportional to the amount of material extruded or by an indicating means rendered responsive to the angular displacement of the handles and which angular displacement is proportional to the linear displacement of the plunger.

In another embodiment of the invention, an adjustable stop or limit plate is mounted on the plunger so as to axially adjust along the length of the plunger to positively limit axial displacement of the plunger during an extruding operation and which limit or stop plate is disposed adjacent to the handle means so that the axial displacement of the plunger can be controlled as the handle means are actuated to control the extrusion of predetermined amounts of dental material.

In another embodiment the dental syringe is adapted to extrude a dental rubber base or other type impression material. This embodiment includes a tubular barrel which defines a reservoir for the dental material and to which there is connected a disposable nozzle tip. A series of spaced ratchet like teeth are formed on the plunger and which ratchet teeth are cooperatively associated with a driving pawl associated with the handle members of the dental syringe. The handle members are pivoted relative to one another so that upon the actuation of the handle members, the plunger is incrementally advanced to extrude the impression material about the tooth; accordingly.

FEATURES

A feature of this invention resides in the provision of a root canal syringe which has a long hyperdermic type needle tip which is capable of being received in the tiny root canals of a tooth and through which a root canal material or resin can be readily extruded to fill the root canal in an effective and positive manner.

Another feature resides in a root canal syringe having a gauge by which a dentist can readily ascertain the amount of filling material being extruded.

Another feature resides in a root canal syringe having a threaded barrel portion to which is threaded an adjustable stop or limit plate, and which stop plate is located between the handle members whereby axial displacement of the plunger can be controlled and predetermined as handles are actuated.

Another feature resides in the provision of a root canal syringe which is capable of exerting the pressures necessary to extrude a viscuous filling material through a miniscule bore of a needle tip with the application of only a nominal force.

Another feature resides in a dental syringe for extruding a filling material in which the plunger is operatively associated with the handle or actuator in a manner so that the filling material is incrementally extruded in predetermined proportional amounts.

Another feature resides in the provision whereby the needle tip is detachably connected to the syringe so as to be rendered readily disposable.

Another feature resides in the provision of concavely shaping the face of the plunger tip so as to enhance the sealing effect between the plunger tip and the walls of the reservoir during an extruding operation.

Another feature of this invention resides in the provision of a dental syringe for precisely positioning an impression material in the small areas of the gums and to cover the tooth so as to remove any air therefrom; before the bulk of the impression material is applied to complete the impression.

Other features and advantages will become more readily apparent when considered in view of the drawings and specifications in which:

IN THE DRAWINGS

FIG. 6 is a sectional side view of a modified form of the invention.

FIG. 7 is a sectional view of still another modified form of the invention, showing the parts in a pre-extruding position.

FIG. 8 is a detail front view of the reservoir fitting of FIG. 7.

FIG. 9 is a detail sectional view showing the needle connection to the reservoir fitting of FIG. 7.

FIG. 10 is a perspective detail view of the reservoir fitting of FIG. 7.

FIG. 11 is a detail perspective view of the needle tip adapted for use in embodiment of FIG. 7.

FIG. 12 is a detail sectional view illustrating a conventional dental syringe needle in its conventional packing tube.

FIG. 13 is a fragmentary side view of a modified detail of the invention.

FIG. 14 is an exploded view illustrating the application of a standard dental needle to a modified embodiment reservoir construction.

DETAIL DESCRIPTION

Figure 1:
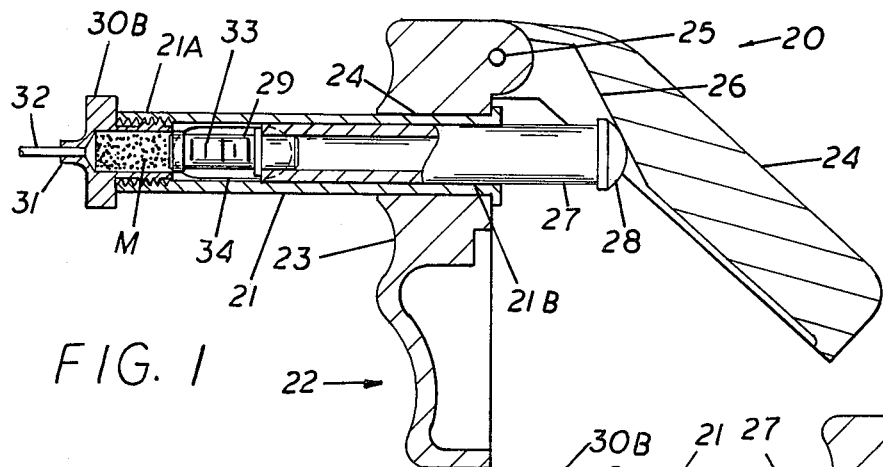
FIG. 1 is a sectional side view of a root canal dental syringe embodying the present invention showing the component parts in a normal operative position.
Figure 2:
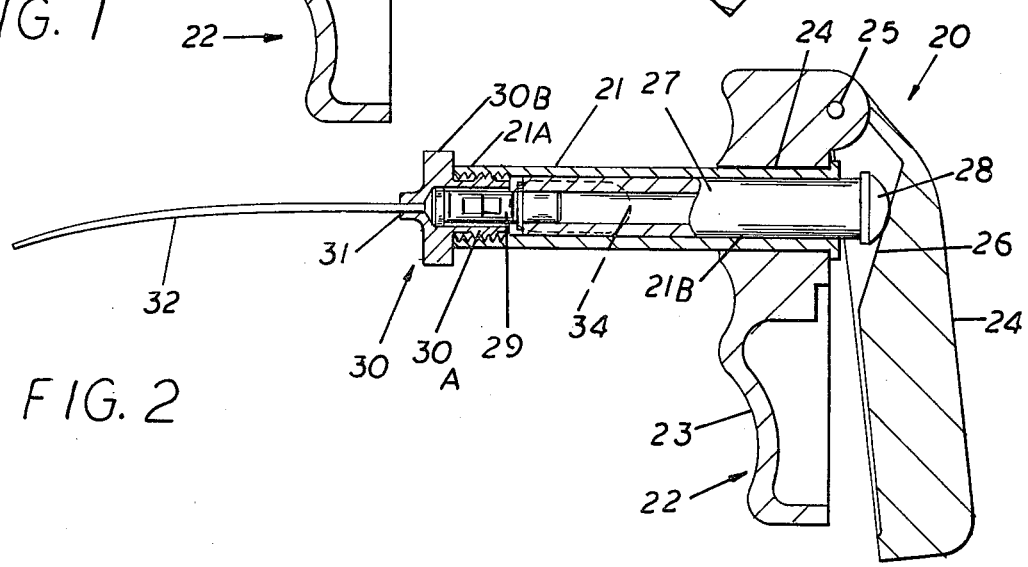
FIG. 2 is a sectional side view of a root canal syringe of FIG. 1 showing the position of the component parts upon completion of an extrusion operation.

Referring to the drawings, there is shown in FIGS. 1 and 2 a dental syringe 20 which embodies the present invention. The dental syringe of FIGS. 1 and 2 is particularly applicable for enhancing the filling of the root canals of a tooth during a root canal procedure. With the improvement of composite resins and various dental filling material; it has been noted that the procedure for performing a root canal operation can be greatly expedited if the tiny root canals of a tooth could be filled with such improved root canal filling material. However, because of the intricacies and/or smallness of a tooth root canal, it was heretofore customary to fill root canals by using "points" which are cemented into the canal.

In accordance with this invention, a root canal syringe 20 is provided to facillitate the placement of a root canal filling material into the root canals of a tooth so as to expedite the filling thereof. As best seen in FIGS. 1 and 2, the root canal syringe 20 comprises an elongated tubular barrel 21 which is suitably connected to a handle assembly 22. The handle assembly comprises a first or fixed member 23 which is provided with a bore 24 for receiving the tubular barrel 21. It will be understood that the tubular barrel 21 is securely fixed to the handle member 23 by any suitable means. As shown, the tubular barrel 21 is provided with a full open front end 21A and a full open rear end 21B. A second or moveable handle member 24 is pivotally connected to the first handle member about a suitable pivot pin 25, as indicated. The moveable handle member 24 is provided with an inclined surface 27 which functions as a cam which engages the rear end of a plunger 27 reciprocally mounted in the bore of the tubular barrel.

Figure 3:
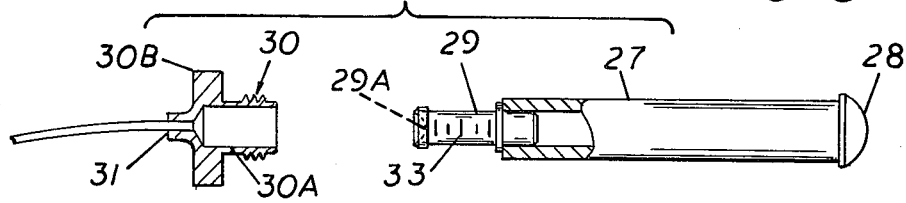
FIG. 3 is a detail exploded view of the plunger and reservoir assembly.

As best seen in FIG. 3, the plunger 27 comprises a hollow stem portion 27A having a cam head 28 at one end which is adapted to extend beyond the end of the tubular barrel. Connected to the other end of the plunger stem 27A is a piston head 29. The face portion 29A of the piston head 29 is formed with a concave or spherical face, which as will be hereinafter described, functions to enhance the extrusion of the root canal filling material M from the dental syringe.

As seen in FIGS. 1 and 2, a reservoir fitting 30 is detachably connected to the open front end 21A of the tubular barrel 21. The reservoir fitting 30 includes an externally threaded cylinder portion 30A which is adapted to be screw threaded into the front end 21A of the tubular barrel. The cylinder portion 30A thus defines a reservoir for containing a supply of the root canal material M to be extruded. It is to be noted that the internal diameter of the cylinder portion 30A of the reservoir fitting 30 is sized so as to snuggly receive the tip end of the piston head 29. Connected to the cylinder portion 30A is a laterally extending flange 30B which defines a means and stop by which the fitting 30 can be screw threaded into the front end of the tubular barrel 21. The fitting 30 is provided with a small outlet opening 31 to which a hyperdermic type needle 32 is fitted. In this form of the invention, the needle 32 is provided with an internal bore and an outer diameter which is sufficiently small so as to be received in the root canal of a tooth. The piston head 29 is proportioned so as to be slightly longer than the length of the reservoir defined by the cylindrical portion 30A of the reservoir fitting 30. Also, as shown in FIG. 3, the piston head is provided with a series of graduations or indica 33 which will function as a gauge or means to ascertain the amount of material which is being extruded. In order that the dentist may view the graduations on the piston head to note the amount of material being extruded, the tubular barrel 21 is provided with a cut out or window 34 adjacent to the inner end of the reservoir fitting.

In operation, it will be apparent to prepare the root canal syringe 20 for an extruding operation, the dentist need only to fill the reservoir portion 30A of the fitting 30 with the appropriate root canal filling material and thereafter screw thread the fitting 30 to the front end of the barrel 21. The plunger 27 and the associated piston head is then inserted through the rear end 21B of the tubular barrel 21 until the face 29A of the piston head is brought to bear upon the filling material M located in the reservoir 30A. Upon squeezing of the handle assembly 22 so that the moveable member 24 is pivoted toward the fixed member 23, the cam surface 26 engaging the cam head 28 of the plunger 27 will effect longitudinal displacement of the plunger where upon the material in the reservoir is extruded through the needle and into the root canal of a tooth.

Because of the spherical or concave confirguation of the piston head face 29A, it will be noted that as the plunger head is advanced into the reservoir, the curvilinear shape of the piston face will cause the material M to be forced outwardly against the internal wall of the reservoir thereby causing the material itself to enhance the sealing effect between the piston head and the internal cylindrical surfaces of the reservoir 30A. Also, the mechanical advantage which is the result of the relatively simple handle assembly enables the relatively viscuous root canal filling material to be extruded through the miniscule bore of the hyperdermic type needle 32, and thereby effectively direct the root canal filling material into the tiny canals of a tooth.

Figure 4:
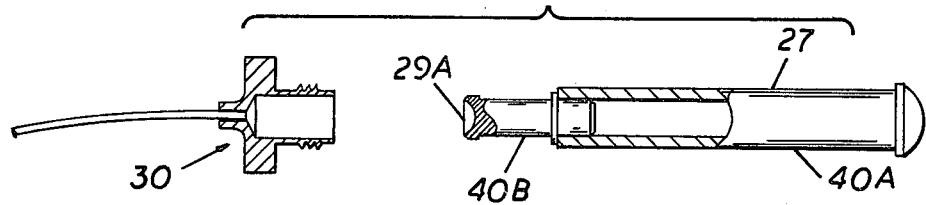
FIG. 4 is an exploded detail view of a slightly modified plunger and needle reservoir assembly partly shown in section.
Figure 5:
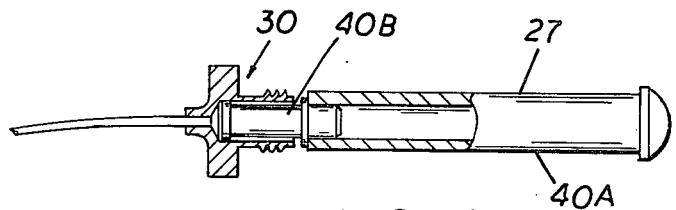
FIG. 5 is a view similar to that of FIG. 4, but showing the relative relationship of the parts after an extruding operation.

FIGS. 4 and 5 are directed to a slightly modified form of the invention. As shown in FIGS. 4 and 5, the plunger 40 comprises the stem portion 40A and a piston head 40B similar to that hereinbefore described. However, in this form of the invention, the piston head is not provided with the graduated marks to indicate the amount of material being extruded during an extruding operation. The associate reservoir fitting 30 is similar to that hereinbefore described.

FIG. 6 illustrates another modified form of the invention. In this form of the invention the dental syringe 50 is provided with a tubular barrel 51 formed with an elongated slot 52 extending longitudinally thereof on the underside thereof. The tubular barrel 51 is suitably connected to a fixed handle member 53, the upper end of which contains a bore 54 for receiving the tubular barrel 51. It will be understood that the tubular barrel 51 can be connected in the bore 54 of the fixed handle member by any suitable means such as by press fit or screw thread. In this form of the invention the plunger 55, which is reciprocally mounted within the barrel, is provided on the under surface thereof with a plurality of longitudinally spaced ratchet teeth 56. The ratchet teeth 56 are disposed in alignment with the elongated slot 52 of the tubular housing 51. A movable handle member 57, which functions as the operating lever, is pivotally connected to the fixed handle member of about pivot pin 57A. A spring 59 for exerting a spring bias on the handle member 53 and 57 is coiled about an anchor pin 60 with one end 59A of the spring engaging a flange 53A on the fixed handle member 53 and the other end 59A of the spring engaging a pin stop 61 connected to the movable handle member 57. The arrangement is such that the spring 59 will normally maintain the handles 53,57 biased under spring tension.

In this form of the invention a ratchet pawl 62 is pivotally mounted on the upper end of the movable handle 57 about the pivot pin 58. As shown, one end 62A of the pawl 62 is arranged to engage the teeth 56 on the plunger. The other end 62B of the pawl 62 is extended past the fixed handle 57 to facilitate a manual displacement of the pawl 62 from the ratchet teeth 56 whenever it is desired to effect the removal of the plunger 52 from the barrel 52. A pigtail spring 63 is coiled about the pivot pin 58 whereby one end engages an anchor pin 64 on the pawl 62 and the other end on pin anchor 65 on the moveable handle 57. The arrangement is such that the ratchet pawl 62 is normally spring biased toward the ratchet teeth 56 of the plunger.

A piston head 66 is connected to the leading end of the plunger 52 and it is similar in construction to that hereinbefore described. Also, the end of the tubular barrel 51 is closed by the reservoir fitting 67 which is also similar to that hereinbefore described.

In this form of the invention it will be apparent that the plunger 55 is incrementally advanced toward the reservoir 67 each time the handles 53 and 57 are squeezed and released. In the embodiment shown it will be apparent that as the movable handle 57 is squeezed to pivot counterclockwise relative to the fixed handle 53, the ratchet pawl 62 will tend to advance the plunger 55 and piston head 66 an incremental amount into the reservoir chamber of the fitting 67. Upon release of the movable handle 57, the spring 59 will normally bias the movable member to its inoperative position and the pawl 62 is reset against the next following ratchet tooth; whereupon the plunger is rendered to be again advanced when the handle members 53 and 57 are again squeezed. On each incremental advance of the plunger, a proportional amount of the material is dispersed through the needle 68.

FIG. 7 illustrates another modified form of the invention. In this form of the invention the dental syringe 70 comprises a tubular barrel 71 and a handle assembly 72 which is similar to that described with respect to FIG. 1; except that in this form of the invention, the plunger 73 and handle assembly 72 is provided with cooperating means whereby a dentist can be apprised as to the amount of material being extruded. As shown in FIG. 7, this is attained by providing the plunger 71 with a series of longitudinally spaced grooves 73 along the rear end portion thereof. The fixed handle member 72A of the handle assembly 72 is provided with a bore 73 which is provided with a seat for retaining a ball detent 74. A compression spring 75 is disposed in the bore 73 to adjustably bias the ball detent 74. A compression spring 75 is disposed in the bore 73 to adjustably bias the ball detent 74 in engagement with the plunger 73 and an adjusting screw 76 or the like is provided whereby the bias of the spring 75 can be readily adjusted.

The movable handle member 72B of the handle assembly 72 is similar to that hereinbefore described, and it is provided with a cam surface 72C, which is adapted to engage the rear head end of the plunger 71.

Connected to the front of the plunger 73 is the piston head 77 similar to that described with respect to FIG. 1.

Connected to the front open end of the tubular barrel 71 is the reservoir fixture 78. In this form of the invention, the reservoir fixture 78 is provided with a laterally extending flange 78A which has axially connected thereto a reservoir chamber 78B. As shown, the reservoir chamber 78B is externally threaded whereby it can be detachably screwed into complementary threads formed internally in the front open end of the barrel 71.

As best seen in FIGS. 8, 9, and 10, the flange portion 78A of the reservoir fitting 78 is provided with a front opening 79 having a laterally extending slotted portion 79A which are adapted to receive the lateral ears 80 connected to the end of a hyperdermic type needle 81, as best seen in FIG. 11.

Behind the face of the reservoir fitting 78 there is provided an arcuate recess 82 which will function to lock the needle 81 in place by a slight relative rotation between the needle and the reservoir fitting. It will, therefore, be apparent from this construction, that the hyperdermic needle 81 can be rendered readily detachable to the flange 78A of the reservoir fitting 78 simply by effecting a relative rotation of the needle a slight angular amount so as to offset the ears 80 from the lateral shots 79A.

In the construction described in FIG. 7, it will be apparent that a dentist can readily ascertain the amount of material being extruded by the clicking sound of the ball detent passing over the grooves 73 as the plunger is incrementally advanced by the squeezing of the handles 72A and 72B.

FIGS. 13 and 14 are directed to a slightly modified form of a reservoir fitting adapted for use with any of the dental syringe embodiments hereinbefore described. The reservoir fitting 90 of FIGS. 13 and 14 is constructed for use with a conventional dental type hyperdermic needle of the type shown in FIG. 12.

In this form of the invention, reservoir portion 90A is externally threaded as hereinbefore described. The flange portion 90B is also similar with the exception that connected to the front side of the flange is a threaded nipple 91. The threaded nipple 91 is adapted to be threadily engaged to a threaded end 92 of a conventional dental hyperdermic needle 93; as illustrated in FIG. 12. Generally, such needles 93 are distributed in their own container 94 which comprises a two part housing. As seen in FIG. 13 with the cap 94A of the container removed, the conventional hyperdermic needle can be readily threaded onto the threaded nipple 91 of the reservoir fitting 90 connected to the barrel of a dental syringe as herein described. Upon securing the hyperdermic type needle 93 to the threaded nipple 91, the needle can be removed from its container as illustrated in FIG. 14.

Figure 15:
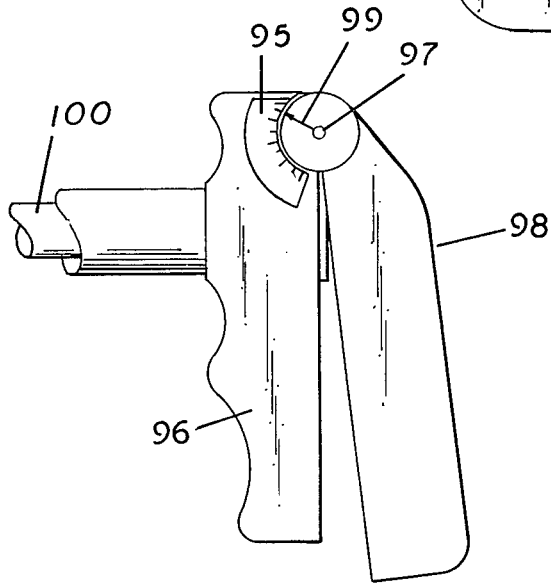
FIG. 15 is a fragmentary view of another modified embodiment.

FIG. 15 illustrates a modified form of dental syringe of the type as indicated in FIGS. 1 and 2. In this form of the invention, a graduated scale 95 is located on the fixed handle member 96 adjacent to the pivot 97 to which the movable or lever handle 98 is connected. Operatively, associated with the movable handle 79 is an indicator 99. It will be understood that the graduation on the scale 95 are rendered proportional to the linear movement of the plunger 100, when the handles 96 and 98 are squeezed. Thus, the amount of material being extruded is rendered proportional to the angular displacement between the relative handle members 96 and 98. It will, therefore, be apparent that the dentist by noticing the scale reading will be able to ascertain the amount of material being dispensed during a desired procedure.

Figure 17:
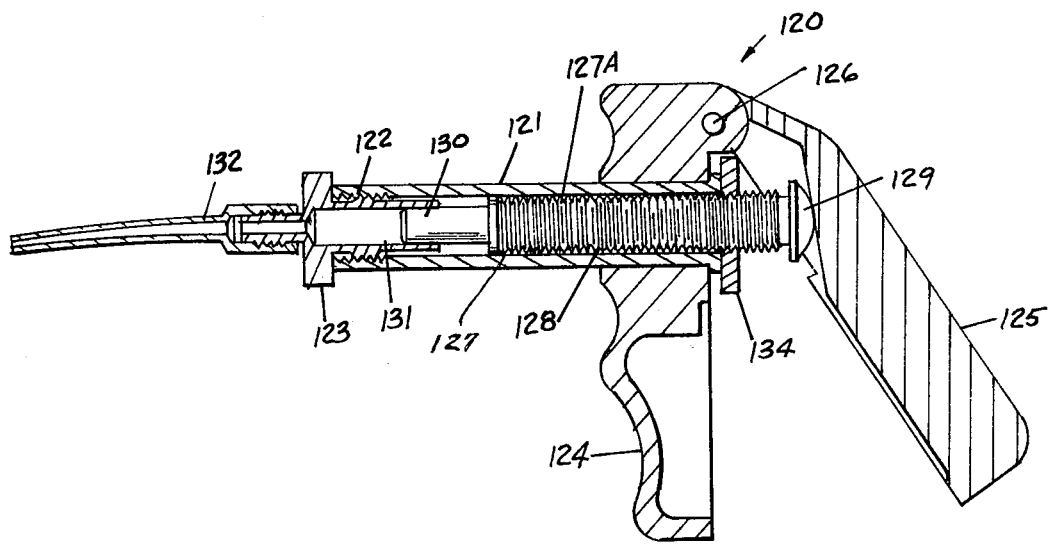
FIG. 17 is a sectional side view of a modified root canal syringe in accordance with this invention.
Figure 18:
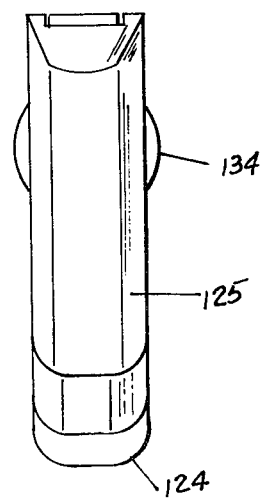
FIG. 18 is an end view of FIG. 17.

FIGS. 17 and 18 are directed to still another embodiment of the invention. The dental syringe 120 illustrated in FIG. 17 comprises a tubular barrel 121 which is open at both ends as hereinbefore described. The forward end of the barrel 121 is internally threaded at 122 and a reservoir fitting 123 is detachably threaded thereto. The reservoir fitting 123 may be similar to any of the fittings hereinbefore described. The barrel has connected thereto a handle member 124 which is fixedly secured to the rear end. As in FIG. 1, the movable handle member 125 is pivotally connected to the fixed handle member 124 by a pin 126.

In this form of the invention the plunger 127 includes a stem portion 127A which is formed with helical external threads 128. The external threads extend over a sufficient portion of the stem portion 127A so as to provide the desired range of adjustments between a minimum and maximum setting. The end of the plunger stem 127A is provided with a cam head 129 at its rear end and a piston head 130 at its forward end. The piston head 130 as hereinbefore described enters the reservoir chamber 131 to extrude the dental material through the connected needle nozzle 132.

In accordance with this form of the invention, a means in the form of a limiting or stop disk or plate 134 is threaded to the end of the barrel. As shown, the disk or plate is provided with a diameter which is sufficiently large so that the peripheral portion thereof extends beyond the side edges of the handle members. The disk or stop plate being threaded on the stem 127A is thus rendered axially displaceable therealong as the disk or plate 134 is rotated relative to the stem in one direction or the other.

In operation the disk or stop plate 134 functions as a stop to limit the displacement of the plunger stem 127A as the handle members 124 and 125 are squeezed. In this manner the dentist can control or limit the amount of material extruded by setting the stop plate or disk 134 to limit the distance that the plunger 127A can be displaced as the handle members are squeezed. With the construction described the dentist is also free to vary the adjustment or the advancement of the plunger in incremental fashion by rotating the stop plate 134 in one direction or the other and thereby control the advancement of the plunger in a dispensing operation. By disposing the stop disk or plate 134 on the stem portion and locating the stop plate between the handle members as shown, the dentist can readily effect the adjustment by using his thumb to effect rotation of the stop plate. Thus, as the handles are squeezed to effect the displacement of the plunger, the dentist with his thumb can incrementally preposition the limit stop by rotating the stop in one direction or another while maintaining pressure in the stem by squeezing the handles 124, 125. The construction described also permits a dentist to extrude the desired amount of root canal material simply by rotating the stop plate 134 in the direction of advancing the plunger. The rotating stop plate 134 thus provides a dentist with an incremental infinite type of adjustment to precisely control the amount of root canal material to be dispersed. Also, by effecting a setting on the stop plate, an initial charge can be dispensed initially to fill the bulk of the root canal, with a fine finishing adjustment being effected by a fine turning of the stop plate to complete the root canal filling operation. The syringe described thus provides a dentist with a tool for effortlessly completing a heretofore, tedius and difficult procedure in a simple and expedient manner.

Figure 16:
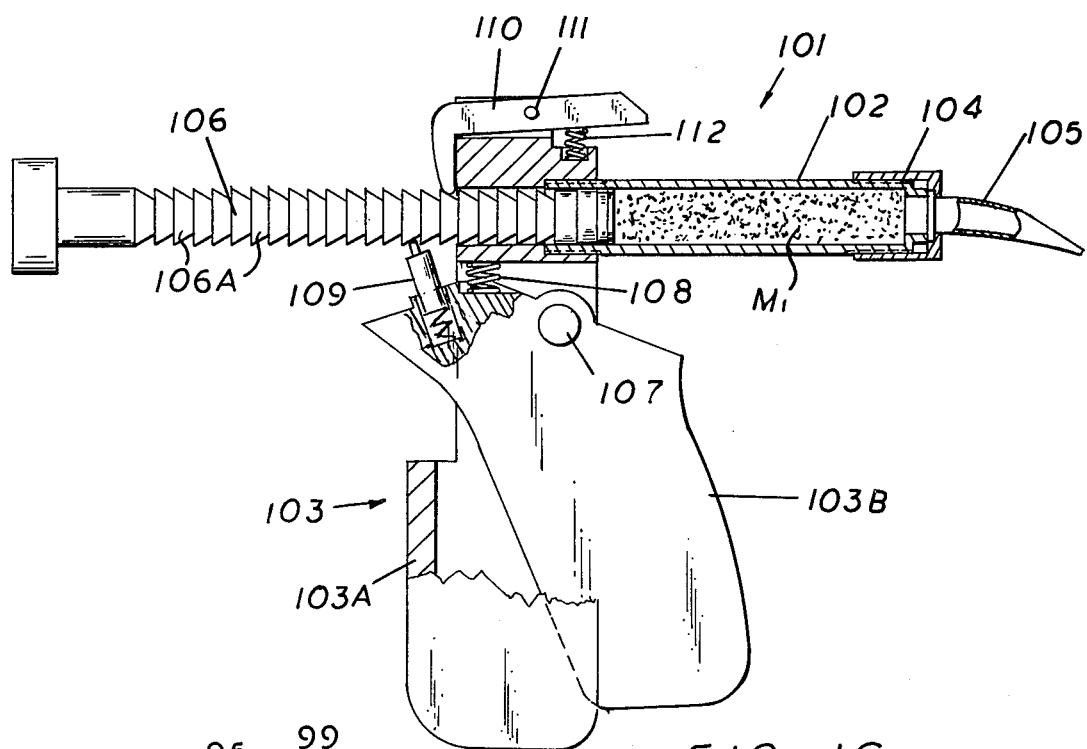
FIG. 16 is a side sectional view of a dental impression syringe embodying the present invention.

FIG. 16 is directed to another modified form of the invention wherein the dental syringe 101 has been modified to render it applicable for dispensing a rubber base or like material such as is utilized for making tooth impressions. As seen in FIG. 16, the dental syringe 101 comprises a tubular barrel 102 which is suitably connected to a handle assembly 103. In the illustrated form of the invention, the tubular barrel 102 may be either press fitted to the fixed handle member 103A, or if desired, it may be threadedly engaged so as to be detachably connected to the fixed handle member 103A of the handle assembly.

Connected to the front end of the tubular barrel 102 is an end cap or fitting 104 which is thready engaged to the barrel. The front cap 104 is provided with a center aperture which is adapted to receive a dispensing nozzle 105 of the type disclosed in my U.S. Pat. Nos. 3,581,399 and 3,900,954. As disclosed therein, the dispensing nozzle 105 comprises a readily disposable plastic tip.

A plunger 106 is inserted through the bore formed in the fixed handle member 103A so as to extend into the bore of the tubular barrel 102. In this form of the invention, the barrel defines the reservoir for containing the rubber base material M to be dispensed in forming an impression.

As best seen in FIG. 16, the plunger 106 is provided with a plurality of longitudinally extending or spaced ratchet like teeth formations 106A.

The handle assembly 103 comprises a fixed bifuricated handle member 103A which has pivotally connected between the bifuricated portions thereof a movable handle 103B. As shown, the movable handle 103B is pivotally connected to handle 103B by pivot pin 107.

A spring 108 is interposed between the fixed handle member 103A and the movable handle member 103B so as to normally maintain a spring bias on the movable handle. Connected to the movable handle 103B is a ratchet pawl 109 which is adapted to engage the ratchet formation 106A formed on the plunger 106. It will be apparent that when the movable handle 103B is squeezed relative to the fixed handle 103A, the ratchet pawl 109 acting on the ratchet like formations 106 of the plunger will cause the plunger 106 to be advanced an incremental amount. Upon each incremental movement of the plunger 106, a proportional amount of material disposed in the reservoir portion of the tubular barrel will be extruded through the nozzle tip 105.

Upon release of the pressure on the movable handle 103B, the spring 108 will normally return the handle 103B to its inoperative position causing the ratchet pawl to be disposed against the next following ratchet formation.

Pivotally mounted adjacent to the upper end of the fixed handle member 103A is a back check lever 110 for restraining the rearward displacement of the plunger as the handle members and the connected ratchet pawl are returned to their normally inoperative position.

As shown, the back check lever 110 consists of a L-shaped member which is pivotally connected about pivot 111 to the fixed handle member 103A. A spring 112 means located in a seat formed in the fixed handle member is disposed in biasing relationship to the horizontal portion of the L shaped back check lever 110.

The other end of the back check lever functions as a pawl to engage the ratchet formation 106A so as to prevent any rearward movement of the plunger as the ratchet pawl 109 is returned to its normal inoperative position. In the construction described, it will be noted that the dental syringe 103 of FIG. 16 provides a positive incremental extrusion of the impression material. With this syringe a dentist is able to precisely locate the impression material about the gums and teeth so as to remove all the air therefrom before the bulk of the impression material is applied to the tooth to complete the impression.

The dental impression syringe as shown in FIG. 16 thus defines a readily compact instrument which is simple to operate, and which enables a dentist to accurately dispense the impression material about a tooth so as to insure that all the air is removed from the tooth before the bulk of the material is applied to make the impression.

While the foregoing invention has been described with respect to several embodiments thereof, it will be readily understood and appreciated that variations and modifications may be made without departing from the spirit or scope of the invention.

What is claimed is:

1. A dental syringe for the placement of a root canal filling material in a root canal of a tooth and for effecting a controlled extrusion of a predetermined amount of said root canal material comprising:
   an elongated tubular barrel having an open front and an open rear end,
   a reservoir fitting means detachably connected to the front end of said barrel, said reservoir fitting means including a chamber for receiving a supply of root canal material to be extruded, said chamber extending into said barrel,
   said chamber having a discharge opening extending forward of said barrel,
   an elongated needle connected to said discharge opening, and having a bore extending therethrough so as to be in communication with said chamber, said needle being sized so as to be received in the root canal of a tooth,
   a plunger reciprocally mounted in said barrel, said plunger including a stem portion and a connected piston head, said piston head being adapted to be snugly received in said chamber as the plunger is axially displaced within said barrel toward said chamber,
   said plunger stem extending beyond the rear end of said barrel,
   a handle means,
   said handle means including a first handle member fixedly connected to said barrel adjacent the rear end thereof,
   a second handle member pivotally connected to said fixed handle member, said second handle member being adapted to bear on said plunger to effect the displacement thereof when said second handle member is squeezed toward said first fixed handle member, whereby a mechanical advantage is exerted by said second handle member on said plunger by the application of a nominal squeezing force on said handle member,
   said plunger stem portion being externally threaded, and an adjustable stop disk threaded on said stem portion, said stop disk being adjustably mounted on said stem portion extending between said handle members whereby said stop disk can be readily adjusted simultaneously with the squeezing of said handle members to effect a controlled extrusion of said root canal material, whereby said stop disk can be variably adjusted along any predetermined length of said threaded portion of said stem to control the amount of extrusion accordingly.

2. A dental syringe for the placement of a root canal filling material in a root canal of a tooth and for effecting a controlled extrusion of a predetermined amount of said root canal filling material comprising:

an elongated tubular barrel having an open front end and an open rear end, a reservoir fitting means detachably connected to the front end of the barrel and disposed in axial alignment therewith, said reservoir fitting means including a chamber for receiving a supply of root canal filling material to be extruded extending into said barrel, an elongated readily disposable hyperdermic type needle connected to the chamber of said reservoir means, said needle having a bore extending therethrough and disposed in communication with said chamber and said needle having an outer diameter sufficiently small so as to be received in the root canal of a tooth, a plunger reciprocally mounted in said barrel, said plunger means including a stem portion and a connected piston head, said piston head being adapted to be snugly received in said chamber as said plunger stem is axially displaced within said barrel toward said reservoir chamber;

a handle means, said handle means including a first handle member fixedly connected to said barrel adjacent to the rear end thereof and disposed normal to the axis of said barrel, said handle member extending to either side of said axis of said barrel, a second handle member pivotally connected to said first handle member to one side of said axis whereby said second handle member is arranged to act on the end of the stem portion to effect axial displacement of said stem portion as said handle members are squeezed toward one another, and an adjustable stop means operatively connected to said stem portion and disposed between said handle members to adjust and limit the forward displacement of said stem portion and connected piston head to determine the amount of root canal material extruded from said chamber, and means for adjustably positioning said stop means along said stem for variably determining the amount of root canal material to be dispensed; said stop means including disk rotatably adjusted along said stem and mounted on said stem portion between said handle members whereby said stop disk can be readily manipulated and rotated by a dentist to adjust said disk axially along said stem as the handle members are squeezed to effect an extrusion by the axial displacement of said plunger, and said ajusting means capable of effecting either incremental axial movement of the disk along said stem portion for adjusting the amount of axial displacement of said plunger means for predetermining the amount of material to be extruded or the entire extrusion of said material.

3. A dental syringe as defined in claim 2 whereby said adjusting means includes an external helical thread formed on the surface of said stem portion adapted to extend between said handle members and said stop disk being threaded on said threaded portion of said stem portion whereby the position of the stop disk relative to said stem portion can be determined by effecting rotation of the stop disk simultaneously with the squeezing of said handle members to effect a controlled displacement of said plunger means so as to control the amount of root canal material being extruded.

4. A dental syringe for the placement of a root canal filling material in a root canal of a tooth and for effecting a controlled extrusion of said root canal filling material comprising:

an elongated tubular barrel having a full open front and rear end, a reservoir fitting means detachably connected to the front end of said barrel and disposed in axial alignment therewith, said reservoir fitting means including a chamber for receiving a supply of root canal filling material to be extruded, and an elongated readily disposable hyperdermic type needle directly connected to said chamber of said reservoir fitting means, said needle having a bore extending therethrough in communication with said chamber and having an outer diameter sufficiently small so as to be received in the root canal of a tooth, a plunger means reciprocally mounted in said barrel, said plunger means extending outwardly through the rear of said barrel, said plunger means including a plunger stem and a connected piston head, said piston head being arranged to be received in said chamber in sealing relationship therewith as said plunger stem is axially displaced toward said chamber, said plunger stem having formed externally thereof a series of longitudinally spaced ratchet like teeth, a handle means connected to said barrel, said handle means including a first handle member having a bore extending therethrough intermediate to the ends of said first handle member, said tubular barrel being fixedly secured in said bore of said first handle member, said first handle member disposed normal to the axis of said barrel, a second handle member pivotally connected to said first handle member, a spring loaded ball stop detent formed in said first handle member for operatively engaging said ratchet like teeth as said plunger is advanced, said teeth being so spaced that an operator can readily ascertain the amount of material extruded, said second handle member including a camming means for engaging the end of said plunger stem whereby said plunger means is advanced into said barrel and connected chamber of said reservoir to extrude the material disposed therein through the bore of said needle when said first and second handle members are squeezed toward one another.

* * * * *